(12) United States Patent
Nakshatri

(10) Patent No.: US 9,200,325 B2
(45) Date of Patent: Dec. 1, 2015

(54) DIAGNOSTIC METHODS AND KIT FOR DETECTING CANCER

(75) Inventor: Harikrishna Nakshatri, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 13/433,722

(22) Filed: Mar. 29, 2012

(65) Prior Publication Data

US 2012/0252907 A1    Oct. 4, 2012

Related U.S. Application Data

(60) Provisional application No. 61/470,855, filed on Apr. 1, 2011.

(51) Int. Cl.
  *C12N 15/11* (2006.01)
  *C12Q 1/68* (2006.01)
  *G01N 33/574* (2006.01)
  *A61K 38/00* (2006.01)

(52) U.S. Cl.
  CPC ........ *C12Q 1/6886* (2013.01); *G01N 33/57415* (2013.01); *A61K 38/00* (2013.01); *C12Q 2600/158* (2013.01); *C12Q 2600/178* (2013.01)

(58) Field of Classification Search
  None
  See application file for complete search history.

(56) References Cited

U.S. PATENT DOCUMENTS

2006/0068434 A1 *  3/2006  Stoerker ........................ 435/6
2009/0291448 A1 * 11/2009  Jurisica et al. ................. 435/6

FOREIGN PATENT DOCUMENTS

WO    WO 2009080437 A1 *  7/2009

OTHER PUBLICATIONS

Veras et al, Inhibition of RNA Polymerase III Transcription by BRCA1, 2009, J.Mol. Biol., 387: 523-531.*
Hansen et al, Expression of CPEB, GAPDH and U6snRNA in cervical and ovarian tissue during cancer development, 2009, APMIS vol. 117, Issue 1, pp. 53-59.*
Hwang et al, U6 upregulation in cancer, Apr. 2010, In: Proceedings of the 101st Annual Meeting of the American Association for Cancer Research; AACR; Abstract 4082.*
Mitchell et al, Circulating microRNAs as stable blood-based markers for cancer detection, 2008, PNAS, vol. 105, 30: 10513-10518.*
Mitchell et al., Proc Natl Acad Sci USA 2008, 105(30):10513-10518.
Lawrie et al., Br J Haematol 2008, 141(5):672-675.
Zhu et al., BMC Res Notes 2009, 2(89): 1-5.
Heneghan et al., Ann Surg 2010, 251(3):499-505.

* cited by examiner

*Primary Examiner* — Mark Shibuya
*Assistant Examiner* — Kate Poliakova-Georgantas
(74) *Attorney, Agent, or Firm* — Stinson Leonard Street LLP

(57) ABSTRACT

The present disclosure is directed to compositions and methods for detecting elevated microRNA U6 concentrations in serum relative to a standard microRNA (e.g. SNORD44) as a diagnostic indicator of metastatic disease. In one embodiment the methods of the present disclosure are used to diagnose the existence of, or assess the risk of, breast cancer in an individual.

6 Claims, 8 Drawing Sheets

DIAGNOSTIC METHODS AND KIT FOR DETECTING CANCER

CROSS REFERENCE TO RELATED APPLICATIONS

This application claims priority to U.S. Provisional Patent Application No. 61/470,855 filed on Apr. 1, 2010, the disclosure of which is hereby expressly incorporated by reference in its entirety.

BACKGROUND

MicroRNAs (miRNA) are a class of multifunctional small (18-25 nucleotides) noncoding RNA molecules. To date, approximately 940 miRNAs have been described. Their functions include epigenetic control of gene expression, mRNA degradation, and suppression of mRNA translation. These diverse functions of miRNAs are necessary for normal development, metabolism, cellular differentiation, proliferation, cell-cycle control, and cell death. Aberrant miRNA expression and/or activity have been implicated in a variety of human diseases including cancer.

Several studies have analyzed miRNA expression pattern in primary tumors of various types, and specific subtypes of cancers could easily be differentiated based on the expression pattern of these miRNAs. Recent studies have identified miRNAs in extracellular space, mainly through a ceramide-dependent secretory exosomes or microvesicles. These secreted miRNAs are functional and enter heterotypic cells to alter migration/invasive properties. However, secretion or packaging of miRNAs into the exosomes is a selective process as the level of miRNA in exosomes secreted by a cell type does not always correlate with the intracellular levels of the corresponding miRNA. Specific cellular proteins, most of them are RNA binding proteins, are suggested to be involved in exosomal secretion of miRNAs and their stability in circulation.

There are several reports describing differential blood/plasma/serum miRNA levels between healthy people and those with various diseases including cancer. Serum miRNA was first reported in diffuse large B-cell lymphoma; sera of patients contained higher levels of miR-155, miR-210, and miR-21. Elevated serum miR-21 levels correlated with good prognosis. Similar studies in prostate cancer revealed elevated levels of miR-141 in the plasma of cancer patients compared to healthy patients, although the same result was not obtained in another study. A four-miRNA predictive profile from serum has been described recently for non-small-cell lung cancer. There are limited studies on breast cancer. One study reported higher serum levels of miR-155 in the progesterone receptor (PR)-positive breast cancer patients compared with PR-negative breast cancer patients. Two recent studies reported elevated levels of miR-195 and let-7a in the whole blood of breast cancer patients; levels of these miRNAs declined after surgical removal of tumors suggesting that they were tumor derived. Elevated levels of miR-195 in the whole blood appear to be unique to breast cancer. Elevated levels of plasma miR-122 and miR-192 were reported after acetaminophen-induced liver injury suggesting that tissues that are enriched for specific miRNAs may release them upon injury.

It is postulated that the miRNAs are released into circulation either actively by the tumor cells or passively as a result of tumor cell death and lysis. However, this does not explain low serum levels of some miRNAs in cancer patients compared with healthy controls. For example, plasma of patients with acute myeloid leukemia show low levels of miR-92a compared with healthy despite of high levels of this miRNA in leukemic cells. In the sera of lung cancer patients, 28 miRNAs are missing and 63 new miRNA species are detectable compared with healthy. Similarly, sera of ovarian cancer patients show elevated levels of five miRNAs and decreased levels of three miRNAs compared with healthy.

These observations raise questions as to whether serum miRNAs in cancer patients are directly derived from tumor cells or an indirect consequence of effects of cancer on other tissues, which then release miRNA into circulation. Considering that the tumor often represents very tiny portion of the body mass, microvesicles/exosomes secreted from the tumor cells are less likely to be sufficient enough to change miRNA profile in a large volume of blood (five liters in a 72-kg person). Systemic effects of cancer on distant organs could easily result in differential serum miRNA profile in cancer patients. More importantly, these changes in serum profile could persist even after the patient is "disease free" if an epigenetic mechanism is involved in the systemic effects. In the latter situation, miRNAs would be poor markers of active disease.

To address the above issues, we determined the levels of breast cancer-associated miRNAs in the sera of healthy and breast cancer patients who are considered clinically cancer-free at the time of serum collection. Further validation of significant initial results were performed with an independent sample set comprising serum from healthy, clinically disease-free breast cancer patients, and patients with overt metastasis and an additional set with serum from healthy and active metastasis patients. We report that SNORD44, a small nucleolar RNA (also called RNU44) is similar in the sera of healthy and clinically cancer-free breast cancer patients in both sets of experiments. However, levels of U6 (also called RNU6-1), which is commonly used for the purpose of normalization between samples, and U6:SNORD44 ratio were elevated in the sera of breast cancer patients, who did not have active disease. Elevated U6 was detected in the sera of both estrogen receptor alpha positive (ER+) and ER-negative breast cancer patients. Sera of patients with overt metastasis also showed elevated U6 or U6:SNORD44 ratio when compared with healthy women. Taken together, these results suggest that elevated U6 serum levels represent persistent systemic effects of breast cancer attained during cancer progression.

SUMMARY

The present disclosure is directed to diagnostic reagents and procedures for the early detection of cancer. More particularly, the present disclosure is directed to methods for analyzing samples to assess the existence of cancerous or pre-cancerous cells. In one embodiment the methods of the present disclosure are used to diagnose the existence of, or assess the risk of, breast cancer.

In accordance with one embodiment, an improved diagnostic screen for detecting and/or monitoring the progression of cancer is provided. Applicants have found that the concentration of some microRNAs that have been used as standards to normalize data between samples when screening for differences in concentration of cancer markers are not constant. In particular concentrations of the microRNA U6 have been found to be elevated in the sera of breast cancer patients, who did not have active disease and in those with overt metastasis. Accordingly, elevated U6 serum levels represent persistent systemic effects of breast cancer attained during cancer progression and thus U6 may not be a good reference molecule for normalizing sample. Alternatively applicants have found that the small microRNA, SNORD44 is similar in the sera of healthy and clinically cancer-free breast cancer patients. Accordingly, the present invention provides an improved method of detecting and/or monitoring the progression of cancer comprising the steps of isolating a serum sample from a subject, determining the concentration of a small microRNA, SNORD44 in said sample, determining the concentration of a breast cancer-associated microRNA (e.g., U6) in said sample and comparing the concentration of said breast cancer-associated microRNA detected in said sample relative to concentrations present in samples from healthy individuals using SNORD44 as a normalization control.

It has been previously suggested that U6 microRNA levels are elevated in is elevated in older individuals compared to healthy youth. Accordingly, the present invention provides an improved method of monitoring aging in individuals, particularly accelerated aging. The method comprises the steps of isolating a serum sample from a subject, determining the concentration of a small microRNA, SNORD44 in said sample, determining the concentration of an accelerated aging-associated microRNA (e.g., U6) in said sample and comparing the concentration of said accelerated aging-associated microRNA detected in said sample relative to concentrations present in samples from healthy individuals using SNORD44 as a normalization control.

In a further embodiment a method of treating cancer is provided wherein a patient is administered an inhibitor of RNAP-III in an amount effective to modulate the activity of RNAP-III to control cancer cell growth and/or the secondary effects of cancer.

In one embodiment a kit for detecting the presence of a breast cancer-associated microRNA is provided wherein the kit comprises materials that can detect the presence and/or expression levels of SNORD44. In a further embodiment the kit also comprises materials that can detect the presence and/or expression levels of U6. Additional materials that may be included in the kit include reagents such as polymerases and PCR primers. In one embodiment the kit is further provided with a reverse transcriptase, a thermostable polymerase, and/or PCR primers for amplifying the U6 microRNA. The kit can be further provided with instructional materials, additional reagents and disposable labware for conducting PCR amplifications.

DETAILED DESCRIPTION

Definitions

Figure 1:
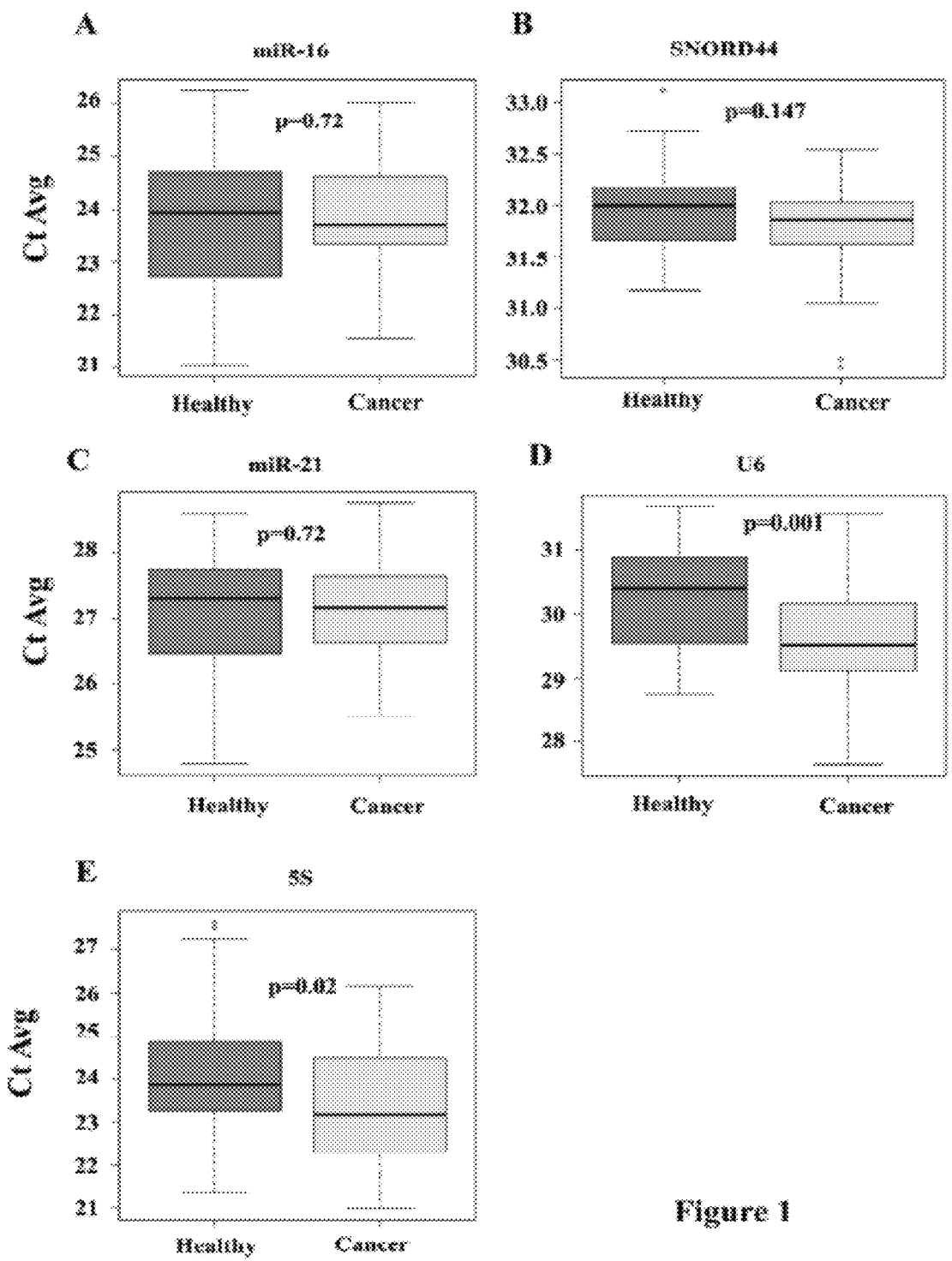
FIGS. 1A-1E are graphs showing the serum concentration levels of U6, 5S, miR-16, miR-21 and SNORD44 in both healthy and cancer patients.

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "isolated" as used herein refers to material that has been removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "purified" and like terms relate to the isolation of a molecule or compound in a form that is substantially free of contaminants normally associated with the molecule or compound in a native or natural environment.

As used herein, the term "primer" refers to an oligonucleotide, whether occurring naturally as in a purified restriction digest product, or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophiles, T. aquaticus, T. lacteus, T.*

*rubens, Bacillus stearothermophilus*, and *Methanothermus fervidus*. Nonetheless, polymerases that are not thermostable also can be employed in PCR assays provided the enzyme is replenished.

The term "label" as used herein refers to any atom or molecule which can be used to provide a detectable (preferably quantifiable) "signal", and which can be attached to a nucleic acid or protein. Labels may provide "signals" detectable by fluorescence, radioactivity, colorimetry, gravimetry, X-ray diffraction or absorption, magnetism, enzymatic activity, and the like.

The term "neoplastic cells" as used herein refers to cells that result from abnormal new growth.

As used herein, the term "tumor" refers to an abnormal mass or population of cells that result from excessive cell division, whether malignant or benign, and all pre-cancerous and cancerous cells and tissues. A "tumor" is further defined as two or more neoplastic cells.

"Malignant cells/tumors" are distinguished from benign cells/tumors in that, in addition to uncontrolled cellular proliferation, they will invade surrounding tissues and may additionally metastasize. Cancer cells are cells that have undergone malignant transformation The term "neoplastic disease" as used herein refers to a condition characterized by uncontrolled, abnormal growth of cells. Neoplastic diseases include cancer.

Embodiments

As disclosed herein there are two critical issues related to circulating miRNAs as biomarkers for detecting breast cancer. The first concerns normalization control and the second relates to the persistence of miRNA changes in patients who are clinically cancer-free. Analysis of candidate miRNAs did not reveal cancer-specific changes in serum profile. However as shown herein, elevated levels of U6 RNA, which is often used for normalization, is found in the sera of both ER/PR-positive and ER/PR-negative breast cancer patients who are under remission. These elevated levels of U6 were detected using SNORD44 as a normalization control. Disease activity did not appear to influence the levels of serum U6 as ER/PR-positive versus ER/PR-negative or node-positive versus node-negative did not show statistically significant difference in U6 levels. Sera of patients with active disease also showed elevated levels of U6.

The above observations raise two important questions; one related to the source of serum U6 RNA and the second related to the mechanism(s) leading to altered U6 levels in serum. It is generally believed that tumor cells are the primary source of serum miRNAs. Reduction of miR-92 in the serum of patients with acute myeloid leukemia, reduction of 28 miRNAs in the serum of lung cancer patients and the observation of elevated U6 RNA in the sera of metastasis-free breast cancer patients as reported herein favor the possibility of cancer altering the release of miRNAs from distant organs or the immune system. The majority of plasma microvesicles are derived from leukocytes; therefore, cancer-induced alteration in leukocyte functions may potentially contribute to miRNA profile changes in the serum of cancer patients.

Our observation of persistent change in U6 levels even after a patient is cancer-free is bit surprising. It is possible that cancer-derived growth factors/cytokines, stress, host response to cancer or carcinogens result in stable epigenetic changes in distant organs. In this context, it is recently reported that chronic stress induces epigenetic changes, which impact DNA methylation patterns and consequent effects on gene expression in both germline and somatic tissues. Furthermore, neonatal experiences altering ERα levels in the adult mammary gland and consequent effects on mammary tumor incidence have been reported using animal models. In addition, a recent study showed a persistent asymptomatic Hepatitis B Virus (HBV) infected individual sharing a similar serum microRNA profile with active HBV infected patients, which is distinct from a healthy individual. Thus, a chronic infection/inflammatory condition may prompt certain organs to undergo permanent change in gene expression pattern. An alternative possibility, which may be provocative, is that upregulation of serum U6 levels is a preamble to cancer initiation or suggestive of a pre-cancerous state, similar to the creation of a niche for metastasis by the VEGFR-1 positive hematopoietic bone marrow progenitor cells before the arrival of cancer cells.

Accordingly, in one embodiment a method of detecting cancer in a patient comprises the steps of determining the concentration of microRNA U6 in a serum sample obtained from a patient and comparing the concentration to population data obtained from health individuals to determine if the microRNA serum concentrations are elevated significantly. In one embodiment the method comprises determining the concentration of U6 in a patient and then using an algorithm to determine the relevance of the raw data. More particularly, the concentration of serum U6 in a patient is inputted into a computer comprising programming for analyzing the concentration of U6 relative to population data established for healthy individuals. The program then analyzes the raw data and produces a conclusion as to whether the detected concentrations of U6 are significantly elevated relative to a normalization control (e.g., the small microRNA, SNORD44), wherein elevated normalized levels of U6, relative to healthy individuals (i.e., a standard curve based on healthy patient population data), are an indicator of an existing precancerous state or current or past cancer. In accordance with one embodiment the method comprises determining the concentration of a small microRNA (e.g. SNORD44) in said sample, determining the concentration of a cancer-associated microRNA (e.g., U6) in said sample and comparing the concentration of said cancer-associated microRNA detected in said sample relative to concentrations present in samples from healthy individuals using SNORD44 as a normalization control.

It has been previously suggested that U6 microRNA levels are elevated in older individuals relative to healthy youth (e.g., individuals 30 or younger). Accordingly, the present invention provides an improved method of monitoring aging in individuals, particularly accelerated aging. The method comprises the steps of isolating a serum sample from a subject, determining the concentration of microRNA U6 in a serum sample obtained from a patient and comparing the concentration to population data obtained from health individuals to determine if the microRNA serum concentrations are elevated significantly. In one embodiment the method comprises determining the concentration of U6 in a patient and then using an algorithm to determine the relevance of the raw data. More particularly, the concentration of serum U6 in a patient is inputted into a computer comprising programming for analyzing the concentration of U6 relative to population data established for healthy individuals. The program then analyzes the raw data and produces a conclusion as to whether the detected concentrations of U6 are significantly elevated relative to a normalization control(e.g., the small microRNA, SNORD44), wherein elevated normalized levels of U6, relative to healthy individuals (i.e., a standard curve based on healthy patient population data), are an indicator of accelerated aging. In accordance with one embodiment the method comprises determining the concentration of a small microRNA (e.g. SNORD44) in said sample, determining the concentration of an accelerated aging-associated microRNA (e.g., U6) in said sample and comparing the concentration of said accelerated aging-associated microRNA detected in said sample relative to concentrations present in samples from healthy individuals using SNORD44 as a normalization control.

RNAP-III transcribes both U6 and 5S RNA. Aberrant RNAP-III-mediated transcription during cancer progression is just beginning to be recognized. RNAP-III upregulation is essential for cMyc-induced transformation. The major signaling pathways activated in cancer including Ras, Raf, PI3K, and AKT enhance, whereas several tumor suppressors including retinoblastoma, PTEN, p53, and BRCA1 decrease RNAP-III activity. Inactivation of BRCA1 alone is sufficient to increase U6 levels in cancer cells. Since elevated U6 levels are present in the sera of patients who are cancer-free at the time of sample collection as well as in the sera of patients with metastasis, alteration in the RNAP-III transcription machinery may be one of the systemic changes that occur during cancer progression prior to diagnosis and treatment. Recent serum protein biomarker profiling studies have shown a "chronic inflammatory state" in breast cancer patients. Whether such inflammatory state alters serum U6 levels by modulating RNAP-III activity is not known. Unlike RNA polymerase II, RNAP-III has not been targeted for cancer therapy. It is not known whether serum U6 influences the course of the disease and if blocking it will impact progression of the disease. In accordance with one embodiment it is anticipated that inhibitors of RNAP-III, that can modulate the activity (but not eliminate) of RNAP-III, can be used to control cancer cell growth and/or the secondary effects of cancer. Alternatively, since elevated U6 levels are observed in patients who are clinically cancer-free, serum U6 levels may serve as a "surrogate marker" for cancer-induced permanent systemic changes, irrespective of the disease course. Distinguishing cancer-associated deleterious systemic changes from insignificant changes is a huge challenge. Nonetheless, additional studies in this direction may help to understand cancer as a systemic disease and potentially to develop treatment strategies targeting "organ component" and "systemic component" of cancer.

In one embodiment a kit for detecting the presence of a breast cancer-associated microRNA is provided wherein the kit comprises materials that can detect the presence and/or expression levels of SNORD44. In a further embodiment the kit also comprises materials that can detect the presence and/or expression levels of U6. Additional materials that may be included in the kit include reagents such as polymerases and PCR primers. In one embodiment the kit is further provided with a thermostable polymerase and PCR primers for amplifying the U6 microRNA. The kit can be further provided with instructional materials, additional reagents and disposable labware for conducting PCR amplifications The reagents of the kit may include buffers and/or the polymerase enzyme. In one embodiment the kit is provided with thermostable polymerase such as the Taq polymerase, for example. In another embodiment the PCR primer provided with the kit is labeled, or reagents are provided for labeling the PCR primer or detecting the amplification product of the reaction. The detection reagents include, for example, DNA binding dyes and labeled probes that bind to U6 RNA. The nucleic acids and other reagents can be packaged in a variety of containers, e.g., vials, tubes, bottles, and the like. Other reagents can be included in separate containers and provided with the kit; e.g., positive control samples, negative control samples, buffers, etc Example 1

Analysis of MicroRNAs in Patient Serum

List of abbreviations: CT, Cycle Threshold; ER, Estrogen Receptor; HBV, Hepatitis B Virus; miRNA, microRNA; Q-PCR, Quantitative Polymerase Chain Reaction; PR, Progesterone Receptor; RNAP-III, RNA Polymerase III; PR Progesterone Receptor Materials and Methods Sample Processing and RNA Extraction All sera were obtained from Indiana University Simon Cancer Center's Komen Tissue Bank. All samples were collected using standard operating procedure, which is detailed in the tissue bank website. RNA was isolated from 250 µL of serum using the mirVana kit (Ambion, Carlsbad, Calif., USA) following the manufacturer's protocol. RNA was eluted with 70 µL of RNase-free water and NanoDrop ND-1000 (Nanodrop, Wilmington, Del., USA) was used to measure the concentration of RNA. Although it was reported previously that serum microRNAs are stable and can withstand repeated freeze-thawing (Mitchell et al, Proc Natl Acad Sci USA 2008, 105(30):10513-10518) consistent results were obtained only when samples from healthy and cancer patients were handled similarly.

Real Time-PCR

In the first series of experiments, five microliter of RNA was reverse transcribed to cDNA in a final volume of 15 µL using Taqman miRNA reverse transcription kit (Applied Biosystems, Carlsbad, Calif., USA). With samples from second and third cohort, 25 ng of RNA was used for reverse transcription. Real-time PCR was performed in duplicate measurements using Taqman universal PCR mix (Applied Biosystems) and specific primers on the q-PCR instrument (Applied Biosystems). Primers for U6 (catalogue number 001973), miR-16 (#000391), miR-21 (#000397), miR-155 (#000479), and miR-195 (#000494) were purchased form Applied Biosystems, whereas 5S primer (#201509) was purchased from Exiqon (Vedbaek, Denmark). SNORD44 primers (MPH01658A-200) were purchased from SABioscience (Frederick, Md., USA). Each amplification reaction was performed in duplicate in a final volume of 20 µL, containing 2 µL of the cDNA. Q-PCR reaction of sera from healthy and cancer patients for a particular probe was in the same plate to limit mechanical errors. The expression levels of miRNAs, U6 and 5S were normalized to SNORD44 or miR-16, and were calculated utilizing the $2^{-\Delta\Delta Ct}$ method.

Statistical Analysis

Expression levels of serum miRNAs were compared using the Mann-Whitney U test. A p-value of less than 0.05 was considered statistically significant.

Results:

Patient characteristics: Table 1 provides details of patient characteristics including age at cancer diagnosis, age at serum collection, tumor types, ER/PR status, and lymph node positivity of the experimental set (cohort #1). Age of healthy volunteers (all women) is also shown. All except one patient were clinically free of overt metastasis at the time of serum collection. Patient characteristics of the second and third validation cohorts are presented in Tables 2 and 3 respectively.

MiRNA and small RNA expression analyses: Earlier studies showing the presence of miR-21 and miR-155 in the serum/plasma of cancer patients (Lawrie et al., Br J Haematol 2008, 141(5):672-675 and Zhu et al., BMC Res Notes 2009, 2:89) prompted us to evaluate their levels in the sera of healthy and breast cancer patients. U6, 5S, miR-16, RNU66, RNU49, RNU19, and SNORD44 levels were also analyzed in these samples to identify a small RNA expressed at a similar level in equal volume of sera from both healthy and cancer patients to serve as a normalization control. Among these, miR-16 has previously been used as a normalization control for serum microRNA profiling studies (Lawrie et al., Br J Haematol 2008, 141(5):672-675). RNU66, RNU48 and RNU19 were undetectable. MiR-16 is one of the most abundant miRNA in the serum (average CT of 24) compared with any other RNAs analyzed, and the abundance of this miRNA in the serum was similar between healthy and cancer patient serum (Table 4 and FIG. 1A). Although SNORD44 was present at lower levels than miR-16 (average CT of 32), its levels were similar in the serum of healthy and breast cancer patients (Table 4 and FIG. 1B). Unlike in diffuse B cell lymphoma, miR-21 did not show any differences between the two groups, although it is an abundant miRNA (average CT of 27) (Table 4, FIG. 1C). Let7f and miR-155 were not considered for further analyses because of higher CT values (>30). In contrast to above RNAs, the levels of U6 and 5S were higher in the serum of cancer patients compared with healthy (Table 4, FIGS. 1D and E). These results provided us the first indication of differential levels of circulating U6 and 5S in cancer patients.

Figure 2:
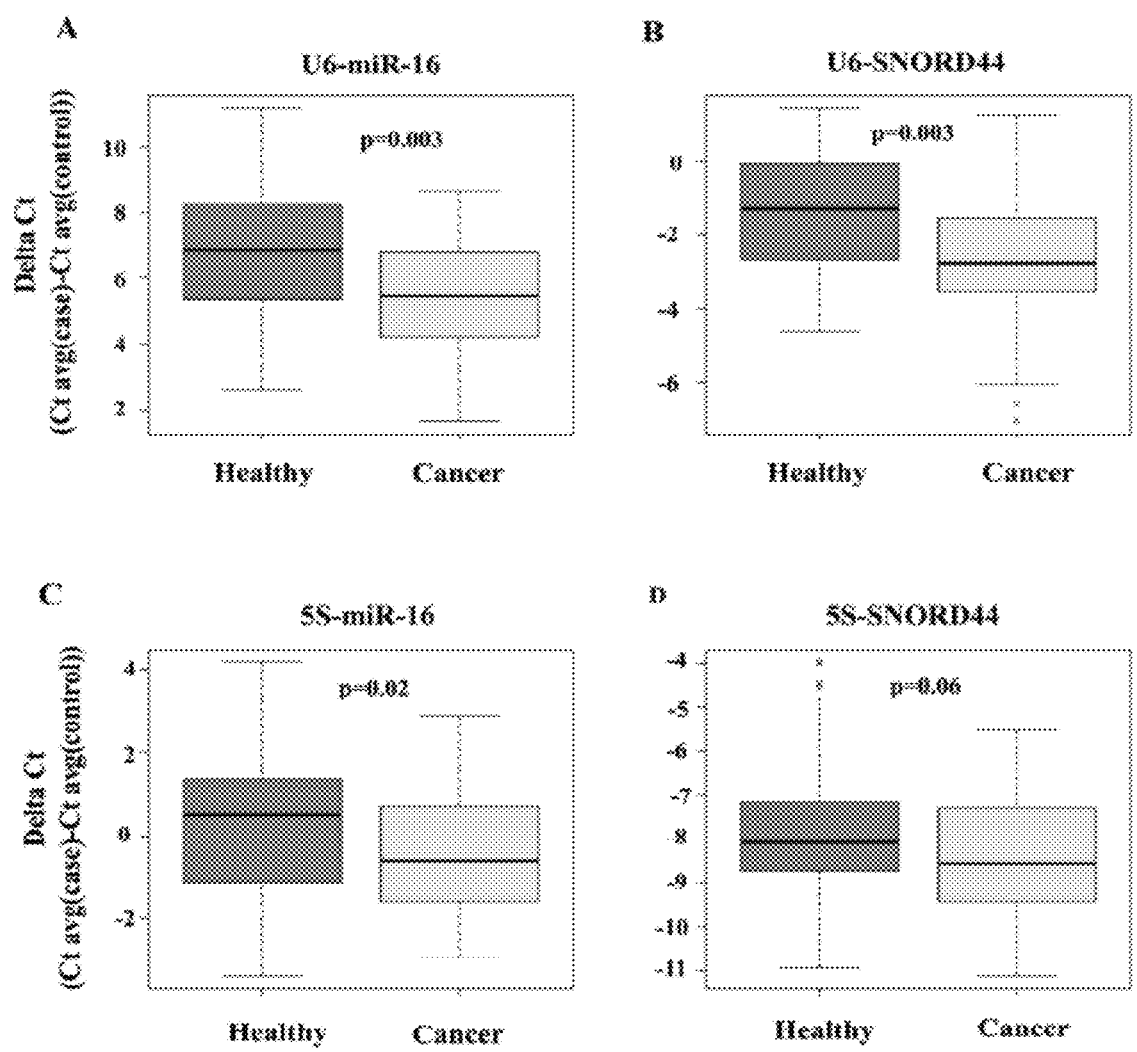
FIGS. 2A-2D are graphs showing the serum concentration levels of U6 and 5S normalized to miR-16 or SNORD44. The levels of U6 and 5S were significantly higher in the sera of cancer patients compared with healthy when miR-16 was used for normalization (FIGS. 2A and 2C). Differences in U6 levels remained significant when SNORD44 was used for normalization (FIG. 2B); however differences in the levels of 5S did not reach significance under similar analysis (FIG. 2D).
Figure 3A:
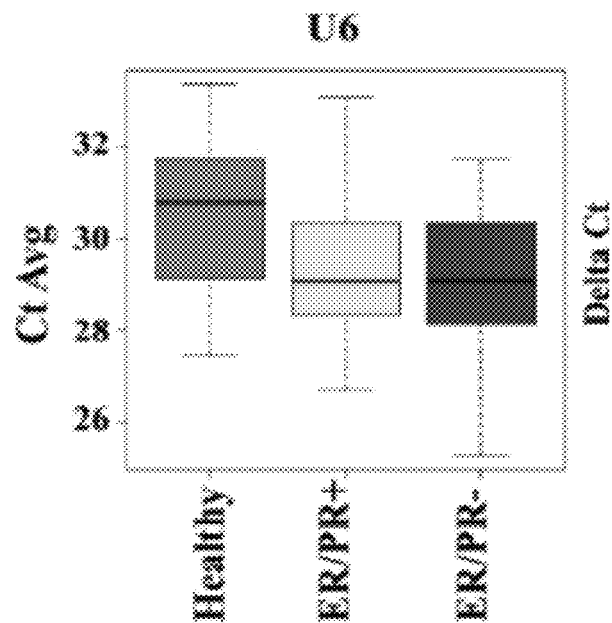
FIGS. 3A-3F are graphs showing the serum concentration levels of U6 and 5S in relation to ER/PR and nodal status of primary tumors. U6 but not 5S levels were higher in the sera of ER/PR-positive breast cancer patients compared with healthy with or without normalization with miR-16 and SNORD44. Despite small sample size, sera of ER/PR-negative patients demonstrated elevated U6 and 5S levels compared with healthy using miR-16 or SNORD44 as internal controls.
Figure 3B:
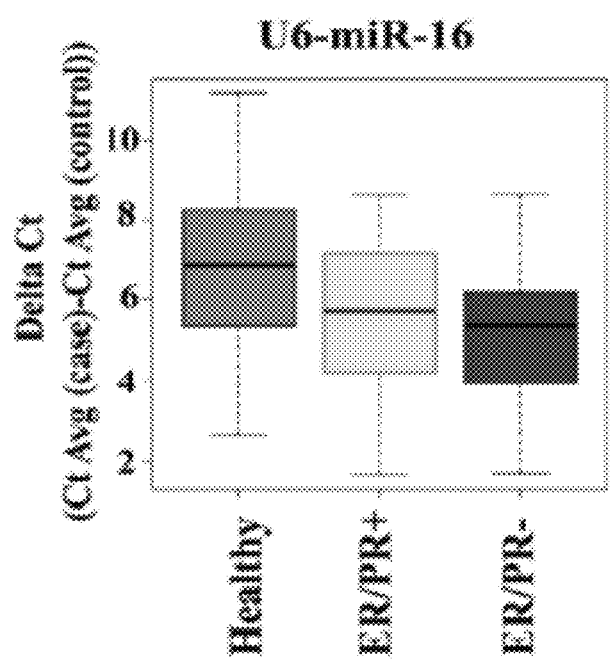
Figure 3C:
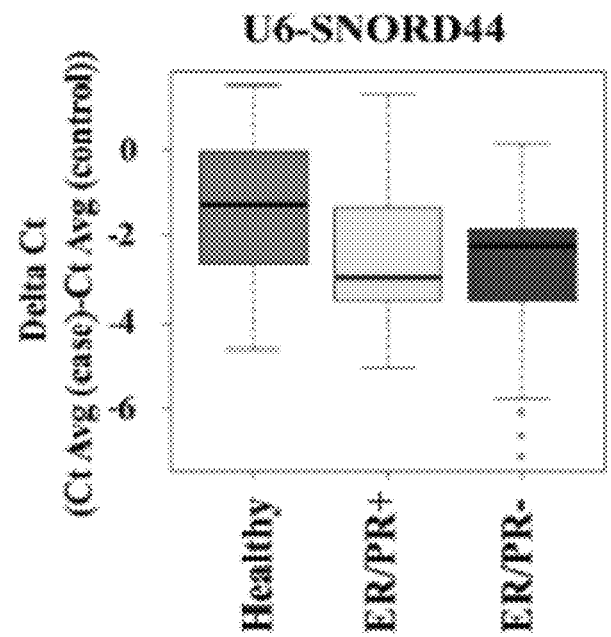
Figure 3D:
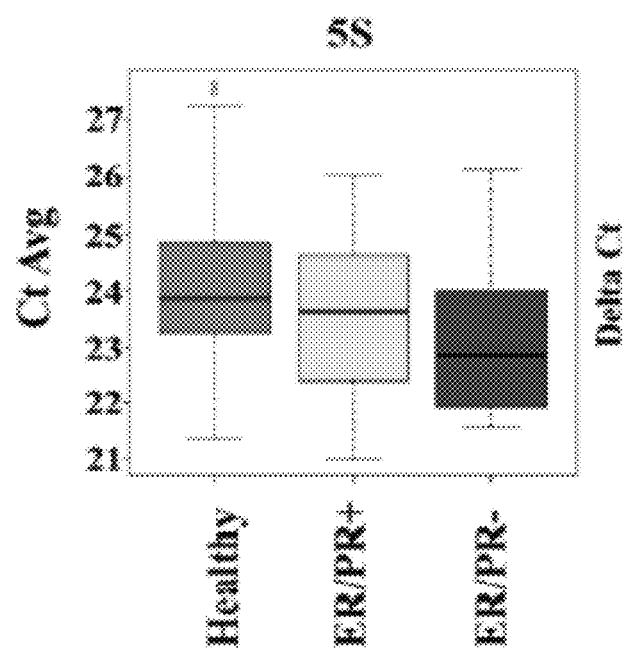
Figure 3E:
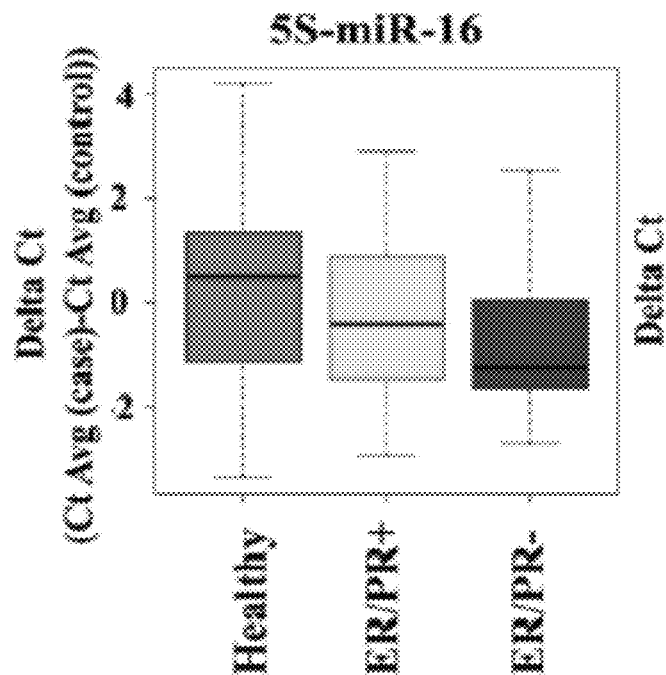
Figure 3F:
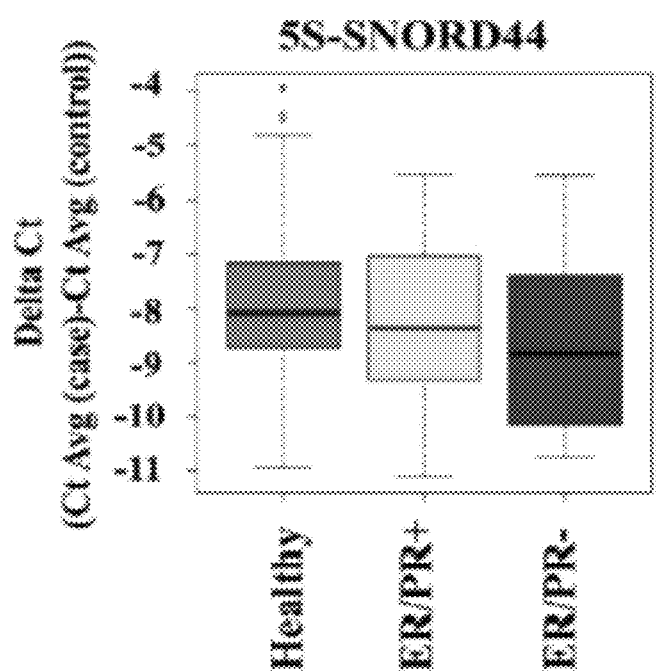

Since miR-16 and SNORD44 levels were similar between two groups, we then determined whether the differences in U6 and 5S levels between healthy and cancer patients retain statistical significance if miR-16 and SNORD44 are used as normalization controls. Indeed, the levels of U6 and 5S were significantly higher in the sera of cancer patients compared with healthy when miR-16 was used for normalization (Table 4, FIG. 2, A-D). Differences in U6 levels remained significant when SNORD44 was used for normalization; however differences in the levels of 5S did not reach significance under similar analysis (Table 4, p=0.06).

Serum U6 and 5S in relation to ER/PR and nodal status of primary tumors: We next determined whether the upregulation of U6 and 5S observed above is unique to specific subtypes of breast cancer. Of 39 patient samples used in the study, ER/PR status of 36 tumors was known; 24 and 12 were ER/PR− positive and ER/PR− negative, respectively. In this subgroup analysis, U6 but not 5S levels were higher in the sera of ER/PR-positive breast cancer patients compared with healthy with or without normalization with miR-16 and SNORD44 (Table 5, FIG. 3). Despite small sample size, sera of ER/PR-negative patients demonstrated elevated U6 and 5S levels compared with healthy using miR-16 or SNORD44 as internal controls (Table 5, FIG. 3). MiR-21 level was similar between healthy and cancer patients of either subtype. Note that the differences in the levels of these RNAs between ER/PR-positive and ER/PR-negative were not statistically significant (data not shown).

Previous studies have shown that lymph node-positive breast cancer patients have lower blood let-7a levels compared with lymph node negative breast cancer patients suggesting the influence of metastasis in regulating serum miRNA levels (Heneghan et al., Ann Surg 2010, 251(3):499-505). In our study, comparison of U6 and 5S RNA between serum of node-positive (n=14) and node-negative (n=23) patients did not reveal any significant difference (data not shown). These results suggest that elevated U6 level observed in the sera of cancer patients who are free of overt metastasis is less likely due to undetectable micrometastasis.

U6 Levels are Elevated in Sera of Breast Cancer Patients Irrespective of Metastasis.

Figure 4A:
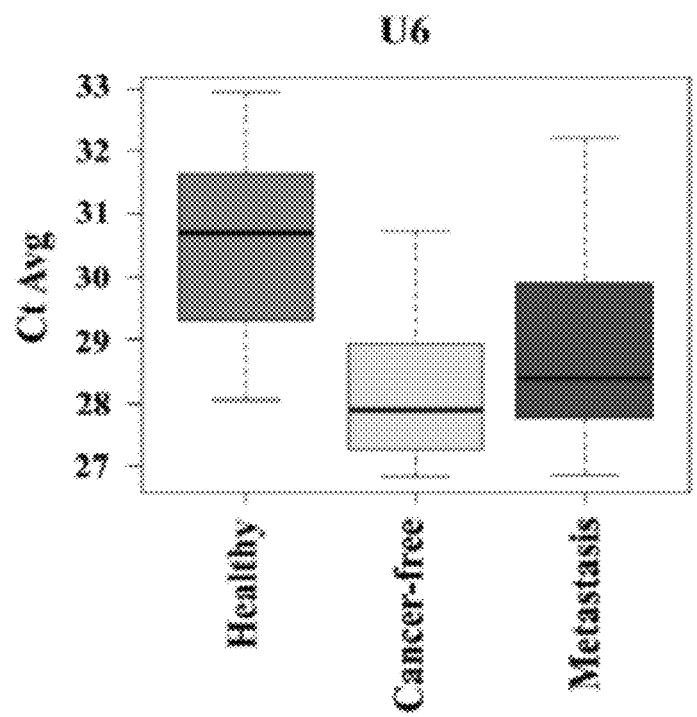
FIGS. 4A-4E are graphs showing the serum concentration levels of U6 in disease-free breast cancer patients and patients with stage 1V metastatic disease. U6 level was significantly elevated in the serum of clinically disease-free breast cancer patients without normalization (FIG. 4A) or with normalization with SNORD44 (FIG. 4B). Unlike the previous experiments, we found a statistically significant increase in miR-16 levels in the serum of disease-free breast cancer patients compared with healthy with or without normalization with SNORD44 (FIGS. 4C and 4D). These results suggest that miR-16 is not appropriate for normalization. When the analysis was restricted to patients with metastasis versus healthy, differences in U6 levels remained significant without normalization and after normalization with SNORD44. Also note that differences in U6 levels between clinically disease-free breast cancer patients and patients with metastasis were not significant. Additionally, SNORD44 levels were similar in all three groups (FIG. 4E).
Figure 4B:
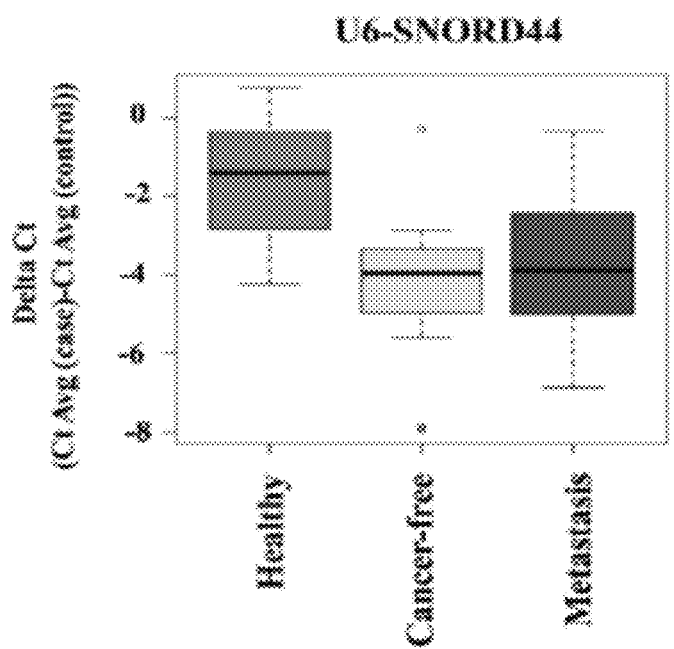
Figure 4C:
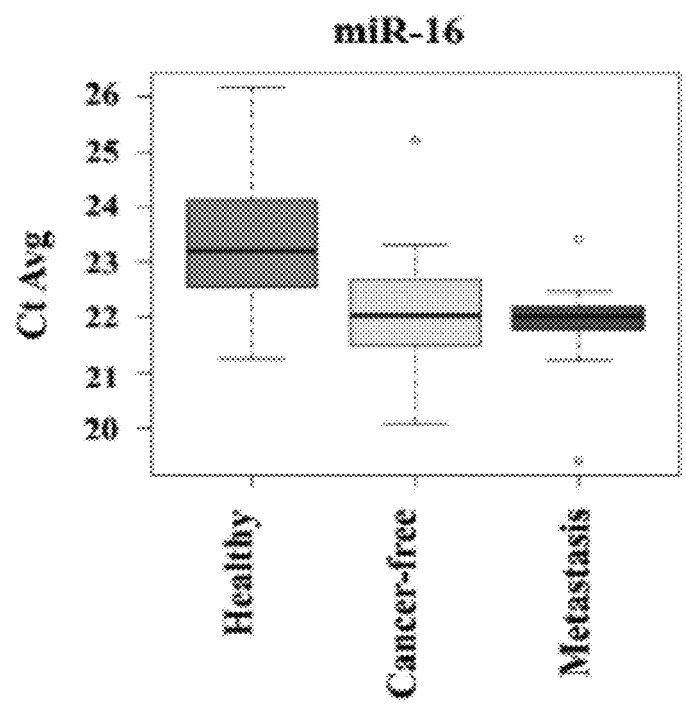
Figure 4D:
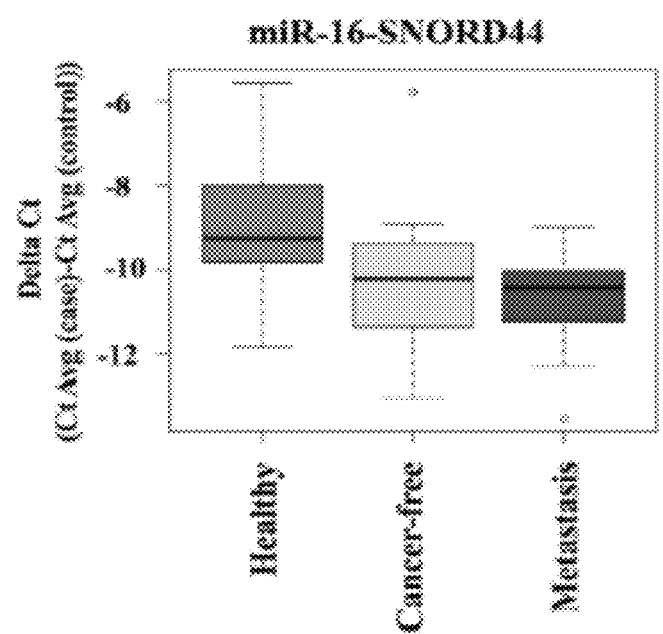
Figure 4E:
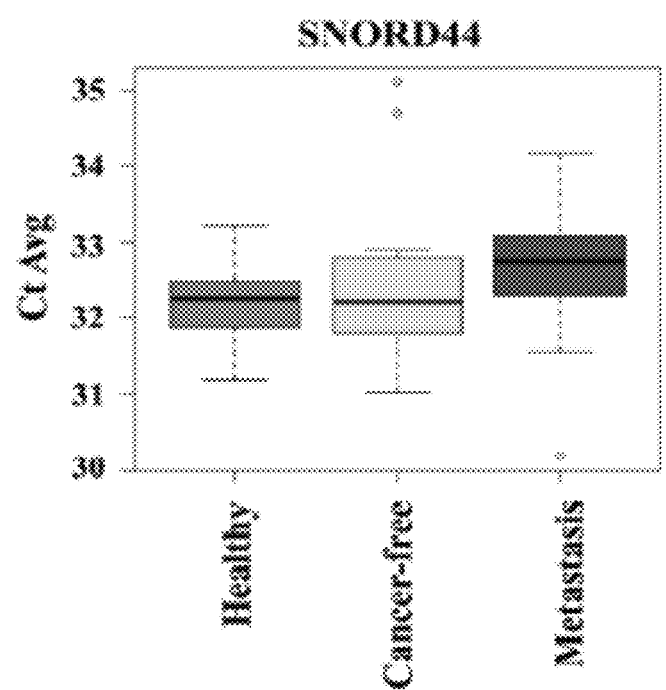

We collected sera from 15 healthy, 15 clinically disease-free breast cancer patients and 15 patients with stage 1V metastatic disease. RNA from three groups was prepared at the same time from equal volume. The cDNA was prepared using 25 ng of RNA and analyzed for the levels of U6, 5S, miR-21, and miR-16. As with the first sample cohort, U6 level was significantly elevated in the serum of clinically disease-free breast cancer patients without normalization (Table 6, FIG. 4A, 5.35 fold p=3.09E-05) or with normalization with SNORD44 (6.6 fold, p=0.00028). Unlike the previous experiments, we found a statistically significant increase in miR-16 levels in the serum of disease-free breast cancer patients compared with healthy with or without normalization with SNORD44 (FIG. 4B). These results suggest that miR-16 is not appropriate for normalization. When the analysis was restricted to patients with metastasis versus healthy, differences in U6 levels remained significant without normalization (Table 6, FIG. 4, 4.31 fold, p=0.0005) and after normalization with SNORD44 (4.8- fold and p=0.004). Also note that differences in U6 levels between clinically disease-free breast cancer patients and patients with metastasis were not significant. Additionally, SNORD44 levels were similar in all three groups (Table 6, FIG. 4C).

The majority of patients in this cohort had ER/PR+ breast cancer. We reanalyzed the above data by considering only ER+/PR+ patients. Significantly elevated U6 or U6:SNORD44 ratio was still observed in cancer-free patients or patients with active metastasis compared to healthy (Table 7).

Analysis of Sera from a Third Cohort of Patients:

To further confirm the results, we analyzed sera from 12 healthy and 18 patients with active metastasis. U6 levels were elevated in the serum of patients with active metastasis, although it did not reach statistical significance, possibly due to smaller healthy sample size (Table 8). However, U6:SNORD44 ratio was significantly elevated in the serum of patients with active metastasis compared to healthy in this cohort. As with the second cohort, we observed significantly elevated miR-16 and miR-16:SNORD44 ratio in patients with active metastasis. However, 5S and 5S:SNORD44 ratio in cohorts two and three were incompatible with results from the first cohort. Taken together, these results reveal reproducible upregulation of serum U6 levels in women who experienced breast cancer irrespective of disease activity at the time of serum collection.

TABLE 1

Healthy Volunteer and Patient characteristics (experimental cohort).

|  | Healthy | All patients | | ER/PR+ | | ER/PR− | |
| --- | --- | --- | --- | --- | --- | --- | --- |
| Number | 40 | 39 | | 24 | | 12* | |
| Age† | | Diagnosis | Analysis | Diagnosis | Analysis | Diagnosis | Analysis |
| Mean: | | 44 | 49.9 | 45.5 | 51.1 | 40.9 | 46.2 |
| Median: | | 43 | 50 | 46 | 53 | 40 | 45 |

TABLE 1-continued

Healthy Volunteer and Patient characteristics (experimental cohort).

| | Healthy | All patients | | ER/PR+ | | ER/PR− | |
|---|---|---|---|---|---|---|---|
| Range | 20-70 | 28-64 | 30-67 | 28-64 | 30-67 | 28-56 | 36-63 |
| Node positive/Negative | N/A | 14/23 | | 8/16 | | 5/7 | |
| Tumor type | N/A | | | | | | |
| Pre-invasive | | 9 | | 5 | | 2 | |
| Invasive | | 28 | | 17 | | 10 | |

Patients in this cohort are clinically disease-free at the time of serum collection
*ER/PR status of remaining three patients is unknown;
N/A—not applicable.
†Age at the time of initial diagnosis and at the time of serum collection for analysis is indicated

15

TABLE 2

Characteristics of healthy volunteers and breast cancer patients during diagnosis and experimental analysis (cohort #2)

A—all patients

| | Healthy | All patients | | Non-metastatic | | Metastatic | |
|---|---|---|---|---|---|---|---|
| Number | 15 | 29 | 1* | 15 | | 14 | 1* |
| Age† | | Diagnosis | Analysis | Diagnosis | Analysis | Diagnosis | Analysis |
| Mean: | 53.26 | 46 | 52.06 | 48.06 | 52.13 | 43.78 | 52 |
| Median: | 53 | 45 | 51 | 48 | 51 | 42 | 53 |
| Range | 47-69 | 23-75 | 23-80 | 38-71 | 46-76 | 23-75 | 23-80 |

B Age at initial breast cancer diagnosis and sample collection of ER/PR+ patients in both non-metastatic and metastatic groups

| | All patients | | Non-metastatic | | Metastatic | |
|---|---|---|---|---|---|---|
| Number | 23 | | 13 | | 10 | |
| Age | Diagnosis | Analysis | Diagnosis | Analysis | Diagnosis | Analysis |
| Mean | 46.34 | 52.08 | 48.69 | 52.38 | 43.3 | 51.7 |
| Median | 47 | 51.0 | 48 | 51 | 42 | 51 |
| Range | 23-75 | 23-80 | 38-71 | 46-76 | 23-75 | 23-80 |

*age and metastatic status of patient is unknown

TABLE 3

Age at cancer diagnosis and sample collection of patients with active disease (cohort #3).

| | All patients with metastasis | | Bone metastasis | | Lung/Liver metastasis | |
|---|---|---|---|---|---|---|
| Number | 18 | | 8 | | 7 | |
| Age | Diagnosis | Analysis | Diagnosis | Analysis | Diagnosis | Analysis |
| Mean | 43.7 | 54.9 | 42.0 | 54.3 | 45.2 | 55.5 |
| Median | 43 | 57.0 | 42 | 54.5 | 43 | 57 |
| Range | 35-58 | 35-78 | 35-49 | 35-78 | 35-58 | 45-62 |

11 of these patients had ER+/PR+ tumors. Metastasis was more common in bone, lung, and liver.

Metastases in three patients were in distant organs other than lung, liver and bone.

TABLE 4

Differences in the levels of U6, 5S, and other RNAs between healthy and cancer patients.

| Small RNA | P value | Fold change (Cancer/Healthy) |
|---|---|---|
| U6 | 0.001 | 2.42 |
| 5S | 0.017 | 1.7 |
| miR-21 | 0.72 | −1.04 |
| miR-16 | 0.72 | −1.06 |
| SNORD44 | 0.147 | 1.08 |
| U6-miR-16 | 0.0047 | 2.58 |
| U6-SNORD44 | 0.0028 | 2.22 |
| 5S-miR-16 | 0.02 | 1.82 |
| 5S-SNORD44 | 0.0599 | 1.53 |
| miR-21-miR-16 | 0.93 | 1.01 |
| miR-21-SNORD44 | 0.36 | −1.14 |

This is the experimental cohort where patients were cancer-free at the time of serum collection.

TABLE 5

Cancer subtype-specific differences in U6, 5S, and other RNAs compared to healthy.

| Small RNA | ER+/PR+ cancer vs Healthy | | ER−/PR− cancer vs Healthy | |
|---|---|---|---|---|
| | P value | Fold change | P value | Fold Change |
| U6 | 0.01 | 2.16 | 0.004 | 3.03 |
| 5S | 0.087 | 1.52 | 0.02 | 2.1 |
| miR-21 | 0.52 | −1.09 | 0.79 | 1.05 |
| miR-16 | 0.614 | −1.11 | 0.962 | 1.01 |
| SNORD44 | 0.21 | 1.09 | 0.29 | 1.09 |
| U6-miR-16 | 0.02 | 2.4 | 0.02 | 3.00 |
| U6-SNORD44 | 0.02 | 2.0 | 0.008 | 2.77 |
| 5S-miR-16 | 0.07 | 1.7 | 0.05 | 2.08 |
| 5S-SNORD44 | 0.196 | 1.4 | 0.055 | 1.92 |
| miR-21-miR-16 | 0.96 | 1.01 | 0.91 | 1.03 |
| miR-21-SNORD44 | 0.273 | −1.19 | 0.85 | −1.04 |

Small RNA levels in the serum of ER+/PR+ or ER/PR− cancer patients were compared with the serum of healthy volunteers (experimental cohort).

TABLE 6

Comparison of expression levels of U6, 5S, and other RNAs in the serum.

| Column ID | P value | Fold change |
|---|---|---|
| *Metastasis versus healthy* | | |
| U6 | 0.0005 | 4.31 |
| U6-SNORD44 | 0.004 | 4.8 |
| miR-16 | 0.001 | 3.4 |
| miR-16-SNORD44 | 0.008 | 3.7 |
| 5S | 0.0058 | −23 |
| 5S-SNORD44 | 0.009 | −21 |
| SNORD44 | 0.708 | −1.1 |
| *Cancer-free versus healthy* | | |
| U6 | 3.68E−05 | 5.35 |
| U6-SNORD44 | 0.00028 | 6.64 |
| miR-16 | 0.0095 | 2.45 |
| miR-16-SNORD44 | 0.015 | 3.04 |
| 5S | 0.02 | −11.0 |
| 5S-SNORD44 | 0.037 | −9.0 |
| SNORD44 | 0.39 | −1.24 |
| *Metastasis versus cancer-free* | | |
| U6 | 0.59 | −1.24 |
| U6-SNORD44 | 0.53 | −1.39 |
| miR-16 | 0.38 | 1.37 |
| miR-16-SNORD44 | 0.67 | 1.23 |
| 5S | 0.51 | −2.06 |
| 5S-SNORD44 | 0.46 | −2.38 |
| SNORD44 | 0.68 | 1.12 |

Comparison was made between healthy and patients with metastasis, healthy and cancer-free, and metastasis and cancer-free (cohort #2).

TABLE 7

ER+/PR+ subgroup specific differences in serum U6, 5S, and other RNAs.

| Column ID | P value | Fold change |
|---|---|---|
| *Metastasis versus healthy* | | |
| U6 | 0.0024 | 3.26 |
| U6-SNORD44 | 0.003 | 4.18 |
| miR-16 | 0.001 | 2.83 |
| miR-16-SNORD44 | 0.002 | 3.65 |
| 5S | 0.0027 | −21 |
| 5S-SNORD44 | 0.007 | −16 |
| SNORD44 | 0.275 | −1.3 |
| *Cancer-free versus healthy* | | |
| U6 | 3.09E−05 | 5.4 |
| U6-SNORD44 | 0.0002 | 6.35 |
| miR-16 | 0.004 | 2.46 |
| miR-16-SNORD44 | 0.01 | 2.9 |
| 5S | 0.05 | −7.2 |
| 5S-SNORD44 | 0.07 | −6.16 |
| SNORD44 | 0.51 | −1.17 |
| *Metastasis versus cancer-free* | | |
| U6 | 0.16 | −1.68 |
| U6-SNORD44 | 0.37 | −1.51 |
| miR-16 | 0.64 | 1.14 |
| miR-16-SNORD44 | 0.55 | 1.27 |
| 5S | 0.268 | −2.93 |
| 5S-SNORD44 | 0.326 | −2.65 |
| SNORD44 | 0.66 | −1.11 |

In this table, sera from patients with ER/PR+ breast cancer were compared with the healthy (cohort #2).

TABLE 8

Differences in the levels of U6, 5S, and other RNAs between healthy and cancer patients (cohort #3).

| Column ID | P value | Fold change |
|---|---|---|
| U6 | 0.26 | 1.54 |
| U6-SNORD44 | 0.043 | 2.28 |
| miR-16 | 0.002 | 2.63 |
| miR-16-SNORD44 | 0.0002 | 3.9 |
| 5S | 0.037 | −2.25 |
| 5S-SNORD44 | 0.25 | −1.52 |
| SNORD44 | 0.0124 | −1.48 |

Patients in this cohort had active metastasis at the time of serum collection.

The invention claimed is:

1. A diagnostic screen for detecting and/or monitoring the progression of breast cancer, the diagnostic screen comprising the steps of:
   isolating a serum sample from a subject suspected of having breast cancer;
   isolating RNA in the serum sample;
   determining the concentration of SNORD44 small nuclear RNA (snRNA) in the subject's sample by amplifying the SNORD44 snRNA in the isolated RNA;

determining the concentration of U6 snRNA in the subject's sample by amplifying the U6 snRNA in the isolated RNA;

normalizing the concentration of the U6 snRNA detected in the subject's sample and the concentration of the U6 snRNA present in samples from healthy individuals, using SNORD44 as a normalization control; and detecting the presence of breast cancer if the normalized concentration of the U6 snRNA in the subject's sample is greater than the normalized concentration of the U6 snRNA in the samples from healthy individuals by a fold change of from about 2 to about 5.

2. The diagnostic screen of claim 1, wherein the detecting step uses a standard curve based on population data of the U6 snRNA concentrations in healthy individuals relative to SNORD44 snRNA concentrations.

3. A method of detecting breast cancer in a patient, the method comprising the steps of:

determining U6 snRNA concentration in a serum sample obtained from the patient suspected of having breast cancer by amplifying the U6 snRNA in the serum sample;

determining SNORD44 snRNA concentration in the serum sample obtained from the patient by amplifying the SNORD44 snRNA in the serum sample;

inputting the determined concentration values into a computer comprising programming for analyzing U6 snRNA concentration relative to population data established for healthy individuals and using detected SNORD44 snRNA concentration as a normalization control, wherein the programming produces a conclusion regarding the probability of the patient having breast cancer.

4. The method of claim 3, wherein the inputting and analyzing step uses a standard curve based on population data of the U6 snRNA concentrations in healthy individuals relative to SNORD44 snRNA concentrations.

5. The diagnostic screen of claim 1, wherein the determining steps are performed with a kit comprising materials that can detect presence of U6 snRNA; and materials that can detect presence of SNORD44 snRNA.

6. The method of claim 3, wherein the determining steps are performed with a kit comprising materials that can detect presence of U6 snRNA; and materials that can detect presence of SNORD44 snRNA.

* * * * *